US00PP15296P2

(12) United States Plant Patent
Schräder

(10) Patent No.: US PP15,296 P2
(45) Date of Patent: Nov. 2, 2004

(54) **VARIETY OF *OSTEOSPERMUM* PLANT NAMED 'SUMOST 01'**

(50) Latin Name: *Osteospermum ecklonis*
Varietal Denomination: Sumost 01

(76) Inventor: Ralf Schräder, Ahronweg 6[a], D-59348, Lüdinghausen (DE)

( * ) Notice: Subject to any disclaimer, the term of this patent is extended or adjusted under 35 U.S.C. 154(b) by 0 days.

(21) Appl. No.: 10/455,848

(22) Filed: Jun. 6, 2003

(51) Int. Cl.[7] ..... A01H 5/00
(52) U.S. Cl. ..... Plt./360
(58) Field of Search ..... Plt./360

(56) References Cited

PUBLICATIONS

UPOV–ROM GTITM Computer Database 2003/02, GTI Jouve Retrieval Software, Citation for 'Sunmost 01'.*

* cited by examiner

*Primary Examiner*—Anne Marie Grunberg
*Assistant Examiner*—Annette H Para
(74) *Attorney, Agent, or Firm*—Webb Ziesenheim Logsdon Orkin & Hanson, P.C.

(57) ABSTRACT

A new and distinct *Osteospermum* plant that exhibits yellow-orange flowers and violet disc florets.

2 Drawing Sheets

Botanical classification: *Osteospermum ecklonis*.
Varietal denomination: 'Sumost 01'.

BACKGROUND OF THE INVENTION

The present invention comprises a new and distinct cultivar of *Osteospermum* plant known by the varietal name 'Sumost 01'. The new variety was discovered in June 2001 in a selected breeding program in Lüdinghausen, Germany designed to produce a new variety of yellow *Osteospermum* that flowers in the summer, is upright and exhibits strong root disease resistance. The new variety was selected from a cross of proprietary unpatented breeding plants, Seedling 2759 (female parent) and Seedling 115/2 (male parent). The new variety exhibits similar flower color to its parents. The new variety has larger flowers and leaves than both parents, and also has a semi-erect habit while both parents are half-hanging. The new variety flowers during the summer similar to 'Seikilrem' (U.S. Plant Pat. No. 13,407), but 'Sumost 01' has larger flowers, a stronger branching habit, a semi-erect habit during the flowering period and overlapping ray florets. The new variety was first asexually reproduced in June 2001 by cuttings in Lüdinghausen, Germany. The new variety has been trial and field tested in Lüdinghausen and has been found to retain its distinctive characteristics and remain true to type through successive propagations.

The following traits distinguish 'Sumost 01' as a new and distinct cultivar:

1. 'Sumost 01' flowers during the summer;
2. 'Sumost 01' flowers without a cool period;
3. No white band is present on the apex of the ray floret;
4. The upper surface flower color is 14A Yellow-orange with a partial 165C Greyed-orange lower surface; and
5. The color of the disc floret is 86A Violet.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
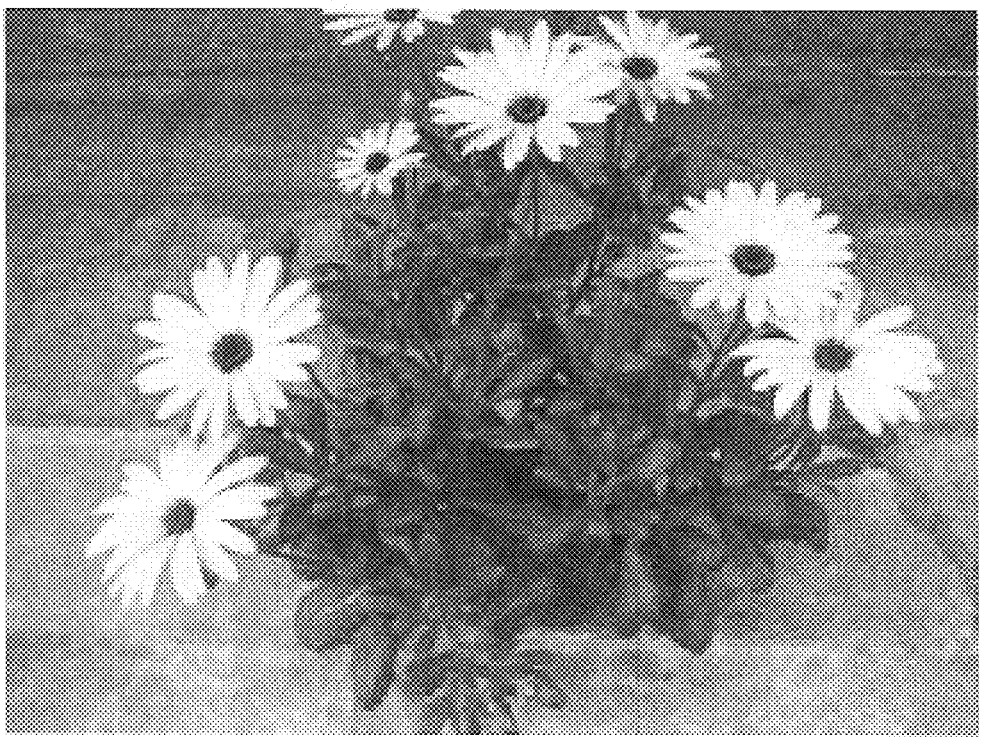
FIG. 1 is a photograph of the plant.
Figure 2:
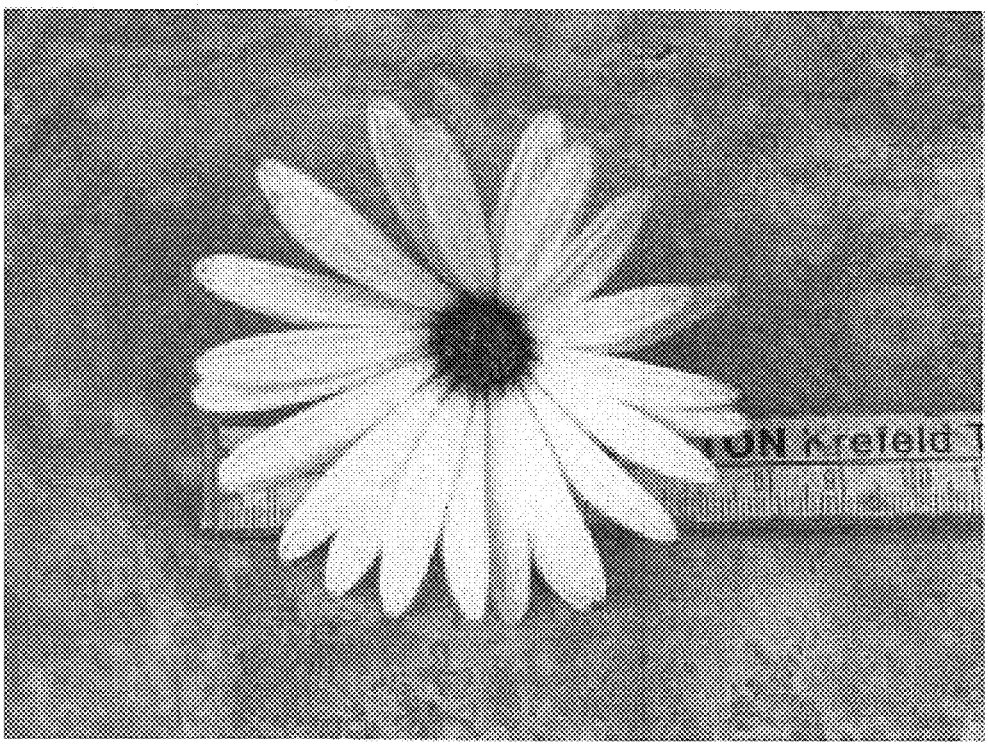
FIG. 2 is a close up view of the blooms of the new plant.

The following detailed description sets forth characteristics of the new cultivar. The data which defines these characteristics were collected by asexual reproductions by cuttings carried out in Lüdinghausen, Germany. Flowering plants were grown in 12 cm containers at temperatures between 14° C. to 16° C. and in a sunny place. Color references are primarily to the 2001 R.H.S. Colour Chart of The Royal Horticultural Society of London.

PLANT

Time to initiate roots: About 4 days at 17° C.
Time to develop roots: About 8 days at 17° C.
Time to produce a finished flowering plant from a rooted cutting: About 12 weeks in a 12 cm container.
Form: Spreading.
Height: Approximately 30–35 cm.
Diameter: Approximately 25 cm.
Vigor: Good before flowering.
Branching habit: Upright; semi-erect at the end of summer.
Lateral branches:
- *Length.*—Primary: 30–35 cm. Secondary: 20–25 cm.
- *Diameter.*—Primary: 8 mm. Secondary: 5 mm.
- *Internode length.*—2.5 cm.
- *Strength.*—Medium.
- *Shape.*—Pentagonal.
- *Pubescence.*—Smooth.
- *Color.*—145A.

Foliage:
- *Arrangement.*—Alternate.
- *Leaf length.*—5.5–6 cm.
- *Leaf width.*—2 cm.
- *Overall shape.*—Obovate.
- *Aspect.*—Weak.
- *Apex.*—Obtuse.
- *Base.*—Obtuse.

*Margin.*—Entire; with some large serration.
*Pubescence.*—None.
*Color.*—Young leaves: Upper surface: 139A. Lower surface: 138A. Mature leaves: Upper surface: 138A. Lower surface: 138B.
*Petiole.*—No petiole present; the leaf is directly connected to the stem.
*Veins.*—Color: Upper surface: 145C. Lower surface: 145C.

FLOWER

Natural flowering season: March to October.
Form: Actinomorphic.
Inflorescence position: Top.
Arrangement: Ray floret overlaps the disc floret.
Number of flowers per plant: Approximately 30.
Size:
*Diameter.*—7.5–8.5 cm.
*Height.*—1.5 cm.
*Disc diameter.*—1.2 cm.
Ray florets:
*Length.*—3.5–4.0 cm.
*Width.*—0.7 cm.
*Shape.*—Long; obovate.
*Apex.*—Obtuse.
*Base.*—Acute.
*Margin.*—Entire.
*Aspect.*—Weak.
*Texture.*—Smooth.
*Number per inflorescence.*—26.
*Color.*—When opening and fully opened: Upper surface: 14A, with a 86A base. Lower surface: 14A, with partial 165C.
Disc florets:
*Length.*—5 mm.
*Width.*—1 mm.
*Shape.*—Tube shaped.
*Number of lobes.*—2.
*Number per inflorescence.*—Approximately 70.
*Color.*—Immature: Apex: 59B. Margin: 1D. Mature: Apex: 59A. Margin: 1D.
Phyllaries:
*Length.*—10 mm.
*Width.*—1 mm.
*Shape.*—Lanceolate.
*Apex.*—Acute.
*Margin.*—Entire.
*Number per inflorescence.*—45.
*Arrangement.*—Overlapping.
*Texture.*—Pubescence present.
*Color.*—Upper surface: 138A with stripes of 138B. Lower surface: 138B.
Peduncle:
*Length.*—Approximately 8 cm.
*Diameter.*—2 mm.
*Color.*—145A.
*Pubescence.*—Present.
*Strength.*—Strong.
Bud (described at 2 days before opening):
*Shape.*—Oval.
*Diameter.*—10 mm.
*Length.*—20 mm.
*Color.*—5A.
Disease resistance: Good resistance against Phytium and Phytophtora.
Fragrance: Faint; sweet.
Temperature tolerance: From 1° C. to 40° C.
Lasting quality: About 6 days with dry weather.
Drought tolerance: Good.

REPRODUCTION ORGANS

Androecium
*Presence.*—On the disc.
*Number.*—Many.
*Filament length.*—3 mm.
*Anthers.*—Shape: Oval. Length: 1 mm. Color: 59A.
*Pollen.*—Color: 29A. Amount: Little.
Gynoecium:
*Presence.*—On the ray florets and some in the disc.
*Pistils.*—Number: Approximately 40. Length: Approximately 3 mm. Style: Length: 2 mm. Color: 155C. Stigma: Shape: Two-parted. Color: N89A.
Seeds:
*Description.*—Irregular production.
*Color.*—161C.
*Length.*—2 mm.
*Width.*—1 mm.
*Number.*—5 to 6.

I claim:

1. A new and distinct variety of *Osteospermum* plant substantially as shown and described.

* * * * *

UNITED STATES PATENT AND TRADEMARK OFFICE

CERTIFICATE OF CORRECTION

PATENT NO. : PP 15,296 P2
DATED : November 2, 2004
INVENTOR(S) : Ralf Schräder

It is certified that error appears in the above-identified patent and that said Letters Patent is hereby corrected as shown below:

Title page,
Item [56], References Cited, PUBLICATIONS, after "Computer Database", "2003/02" should read -- 2003/01 --

Signed and Sealed this

Twelfth Day of April, 2005

JON W. DUDAS
*Director of the United States Patent and Trademark Office*